(12) United States Patent
Jeong et al.

(10) Patent No.: US 8,980,293 B2
(45) Date of Patent: Mar. 17, 2015

(54) COSMETIC COMPOSITION CONTAINING RETINOL STABILIZED BY POROUS POLYMER BEADS AND NANOEMULSION

(75) Inventors: Sang-Ho Jeong, Gyeonggi-do (KR); Ji-Hyun Son, Seoul (KR); Su-Jin Jang, Gyeonggi-do (KR); Yun-Jeong Kim, Gangwon-do (KR); Jong-Woo Cheon, Gyeonggi-do (KR)

(73) Assignee: Act Co., Ltd., Chungcheongbuk-do (KR)

( * ) Notice: Subject to any disclaimer, the term of this patent is extended or adjusted under 35 U.S.C. 154(b) by 265 days.

(21) Appl. No.: 13/805,117

(22) PCT Filed: Apr. 28, 2011

(86) PCT No.: PCT/KR2011/003132
§ 371 (c)(1), (2), (4) Date: Dec. 18, 2012

(87) PCT Pub. No.: WO2011/162478
PCT Pub. Date: Dec. 29, 2011

(65) Prior Publication Data
US 2013/0095157 A1    Apr. 18, 2013

(30) Foreign Application Priority Data
Jun. 21, 2010 (KR) .......................... 10-2010-0058549

(51) Int. Cl.
| | | |
|---|---|---|
| *A61K 8/67* | (2006.01) | |
| *A61K 8/11* | (2006.01) | |
| *A61K 31/07* | (2006.01) | |
| *A61K 9/51* | (2006.01) | |
| *A61Q 19/08* | (2006.01) | |
| *A61K 8/37* | (2006.01) | |
| *A61K 8/55* | (2006.01) | |
| *A61K 8/81* | (2006.01) | |
| *A61K 8/97* | (2006.01) | |
| *A61K 8/02* | (2006.01) | |
| *A61K 8/06* | (2006.01) | |

(52) U.S. Cl.
CPC . *A61K 8/11* (2013.01); *A61K 8/671* (2013.01); *A61K 9/51* (2013.01); *A61K 31/07* (2013.01); *A61Q 19/08* (2013.01); *A61K 8/375* (2013.01); *A61K 8/553* (2013.01); *A61K 8/8152* (2013.01); *A61K 8/97* (2013.01); *A61K 8/0279* (2013.01); *A61K 8/06* (2013.01); *A61K 2800/21* (2013.01); *A61K 2800/52* (2013.01)
USPC ............... 424/401; 424/63; 424/451; 424/64; 424/49; 424/70.11; 514/725

(58) Field of Classification Search
USPC ......................................................... 424/401
See application file for complete search history.

(56) References Cited

U.S. PATENT DOCUMENTS

2003/0232091 A1* 12/2003 Shefer et al. .................. 424/490
2004/0096419 A1    5/2004 Golz-Berner et al.

FOREIGN PATENT DOCUMENTS

| JP | 2008-105952 A | 5/2008 |
|---|---|---|
| KR | 1020040021593 A | 3/2004 |
| KR | 1020050028544 A | 3/2005 |
| KR | 1020090009722 A | 1/2009 |

OTHER PUBLICATIONS

Ahn et al. Derwent Acc. No. 2003-741876. KR 2003042527, published Jun. 2, 2003, abstract translation.*
International Search Report for PCT/KR2011/003132, Feb. 2012. (See NPL document in IDS filed Dec. 28, 2012).*
International Search Report: mailed Feb. 6, 2012; PCT/KR2011/003132.

* cited by examiner

*Primary Examiner* — Audrea Buckley
(74) *Attorney, Agent, or Firm* — Ladas & Parry LLP

(57) ABSTRACT

The present invention relates to a method for stabilizing retinol (Vitamin A), an unstable fat-soluble material, to use the same in cosmetics. The present invention provides an anti-inflammatory and skin wrinkle reducing cosmetic composition containing retinol stabilized by nano-emulsification, wherein a retinol polymer nanocapsule formed by capturing retinol with porous polymer particles is nano-emulsified by a mung bean MCT (medium chain triglyceride) extract and lecithin for stabilizing retinol.

9 Claims, 4 Drawing Sheets

RESULTS OF STABILITY TEST AT 45°C

RESULTS OF STABILITY TEST AT 45°C

| | EXAMPLE 2 | COMP. EXAMPLE 4 | COMP. EXAMPLE 5 |
|---|---|---|---|
| INITIAL STAGE |  |  |  |
| 1 WEEK |  |  |  |
| 2 WEEKS |  |  |  |
| 3 WEEKS |  |  |  |
| 4 WEEKS |  |  |  |
| 5 WEEKS |  |  |  |

COSMETIC COMPOSITION CONTAINING RETINOL STABILIZED BY POROUS POLYMER BEADS AND NANOEMULSION

TECHNICAL FIELD

The present invention relates to a technology for using retinol, an unstable fat-soluble substance, in cosmetics by stabilizing the retinol, and, more particularly, to a technology for using retinol (vitamin A), a bioactive component, in low-irritation cosmetics for improving a skin wrinkle reducing effect, wherein the retinol is primarily stabilized by adsorbing the retinol in mesoporous polymer particles, and is then secondarily stabilized by nano-emulsifying the retinol using a specific fat-soluble natural extract and lecithin.

BACKGROUND ART

The term "cosmeceuticals" is a compound word comprised of the words "cosmetics" and "pharmaceuticals." Recently, the development of cosmeceuticals has received concentrated attention. Research into functional active ingredients, research into formulations related to the acceleration of transdermal absorption of effective ingredients, and basic research into skin physiology has actively been conducted. Thus, research into the development of functional ingredients related to the prevention of skin aging, the protection of skin from external environmental factors such as ultraviolet rays, and the acceleration of creation of new skin cells, research into the efficacy thereof, and research into methods of measuring skin stability using the same have attracted considerable attention. Examples of the effective ingredients being intensively researched as raw materials of cosmetics may include vitamin A, C, E and the like, ceramide, $\alpha$-hydroxy acid, $\beta$-hydroxy acid, glucan, enzymes, modulators, various plant extracts, and the like.

Vitamins have been commonly used for centuries to prevent or decrease skin wrinkles, and basic research into the influence of vitamins on skin has been actively conducted. However, it is difficult to variously apply vitamins because they have low stability. For this reason, research into improving the stability of vitamins themsemselves has been conducted in combination with the aforementioned basic research. Particularly, research into retinol, vitamin A, has been actively conducted over the last ten years. It is reported that retinol is effective at accelerating the synthesis of collagen in skin and accelerating the creation of cells by prompting the turnover of the stratum corneum. However, retinol is problematic in that strong skin irritancy is caused when an excessive amount of retinol is applied to skin, and in that retinol itself is very unstable. Therefore, there is required a formulation technology which can accelerate the transdermal absorption of retinal and can continuously and uniformly apply retinol to the skin such that the stability of retinol is improved and the activity of retinol is sufficiently and effectively exhibited even when a small amount of retinol is used. In order to solve the above problem, currently, research into encapsulation, anhydrous bases, and special container development is being conducted, and, particularly, research into the encapsulation of retinol using a polymer is being variously conducted both at home and abroad.

For example, Korean Patent Registration No. 0463167 discloses a transdermal absorbent, wherein retinol, as a bioactive ingredient, is captured in polymer particles each having a size of several nanometers to several hundreds of nanometers, and the polymer particles diffuse and permeate into the skin to allow the polymer particles provided with the bioactive ingredient to stay in an intermediate layer of a skin structure, so the bioactive ingredient included in the polymer particle is slowly transferred into the skin.

However, as described above, when retinol is captured in polymer particles and then directly diffuses and permeates into the skin, there is a problem in that the skin is irritated, and the stability of retinal in a formulation cannot be sufficiently assured. The present inventors found that, when retinol is primarily adsorbed on mesoporous polymer beads, the mesoporous polymer beads including retinol are secondarily formed into retinol capsules using a stabilization technology for forming nano-emulsions, and then when the retinol capsules are used in cosmetics, the stability of retinol is greatly improved, thereby making it possible to manufacture cosmetics whose transdermal absorption is accelerated, whose skin irritancy (the greatest problem of retinol) is reduced and whose skin wrinkle reducing effect is improved. Based on this finding, the present invention was completed.

DISCLOSURE

Technical Problem

Accordingly, an object of the present invention is to provide a cosmetic composition including retinol stabilized by a doubly stabilizing method.

Another object of the present invention is to provide a method of effectively stabilizing retinol.

Technical Solution

In order to accomplish the above objects, an aspect of the present invention provides an anti-inflammatory and skin wrinkle reducing cosmetic composition containing retinal stabilized by nano-emulsification, wherein a retinol polymer nanocapsule formed by adsorbing retinol with mesoporous polymer beads is nano-emulsified to a size of 50~200 nm using a mung bean MCT (medium chain triglyceride) extract, which is a fat-soluble natural extract, and lecithin to stabilize the retinal.

The mesoporous polymer beads may have excellent biocompatibility, and may be made of polymethylmethacrylate crosslinked with ethyleneglycol dimethacrylate. The retinol, which is an active ingredient, may be included in the retinol polymer nanocapsule in an amount of 0.5~10 wt %.

The lecithin may be at least one selected from the group consisting of hydrogenated lecithin, phosphatidylcholine, phospholipid, hydrogenated lysophosphatidylcholine, hydrogenated lysolecithin, hydroxylated lecithin, and unsaturated lecithin. Preferably, the lecithin may be hydrogenated lysophosphatidylcholine. The nano-emulsion may have a size of 50~200 nm, preferably, 70~100 nm.

The stabilized retinol may be included in an amount of 0.0001 wt %~50 wt % based on the total amount of the cosmetic composition. The formulation of the cosmetic composition may be applied to soft wash, nutritive wash, massage cream, nutritive cream, skin packs, gel, skin cream, lipstick, makeup base, foundation, shampoo, rinse, body cleanser, soap, toothpaste, oral purifier, lotion, ointment, patches, or spray.

Another aspect of the present invention provides a method of stabilizing retinol, including the steps of: (A) (a1) adding mesoporous polymer beads having a particle size of 50 nm to 500 nm to ethanol to prepare a first mixture, stirring the first mixture, mixing an antioxidant (butylated hydroxytoluene) with the first mixture to prepare a second mixture, and then dissolving the second mixture, (a2) adding retinol (vitamin A)

to the second mixture to prepare a third mixture, completely dissolving the third mixture, mixing the third mixture with distilled water to prepare a mixed solution, and then stirring the mixed solution, (a3) filtering and drying the mixed solution under reduced pressure to prepare a retinol-adsorbed polymer nanocapsule; (B) (b1) heating glycerin, and then mixing the heated glycerin with tocopheryl acetate, butylated hydroxyanisole and a mung bean MCT extract to prepare a fourth mixture while dissolving the fourth mixture, (b2) adding cholesterol to the fourth mixture to prepare a fifth mixture, dissolving the fifth mixture, and then adding the retinol-adsorbed polymer nanocapsule to the fifth mixture to prepare a sixth mixture, (b3) adding hydrogenated lysolecithin to the sixth mixture to prepare a seventh mixture, dissolving the seventh mixture, adding purified water to the seventh mixture to prepare a mixed solution, and then stirring the mixed solution to prepare a nano-emulsion composition; and (C) forming the nano-emulsion composition into a nano-emulsion having a size of 50~200 nm using a high-pressure homogenizer (microfluidizer) to stabilize retinol.

In the method, the nano-emulsion composition may inlcude 1~60 wt % of glycerin, 0.5~1 wt % of tocopheryl acetate, 0.03~0.05 wt % of butylated hydroxyanisole, 1~12 wt % of a mung bean MCT (medium chain triglyceride) extract, 1~2 wt % of cholesterol, 1~10 wt % of a retinol polymer nanocapsule, 1~3 wt % of hydrogenated lysolecithin, and purified water.

Advantageous Effects

The cosmetic composition containing stabilized retinol according to the present invention is effective in that its stability is high because dually stabilized retinol is used, its transdermal absorptivity is excellent, its sustained-release is excellent because retinol is captured in predetermined-sized polymer nanocapsules and then permeated into the skin, and thus active ingredients are continuously supplied into the skin, thereby reducing skin wrinkles.

BEST MODE

Figure 1:
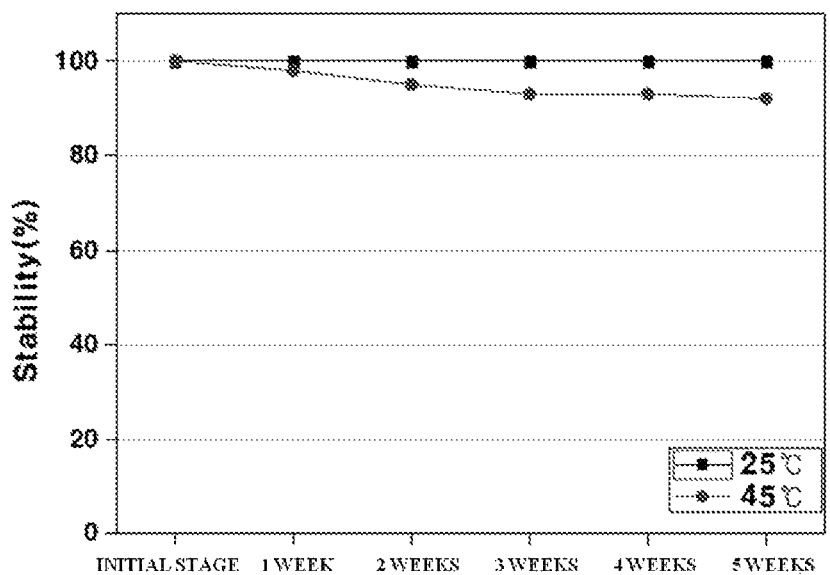
FIGS. 1 and 2 are graphs showing the titer maintaining ability of the stabilized retinol of the present invention.

The present invention is technically characterized in that retinol, which is an active ingredient unstable to moisture or heat, is effectively stabilized, and the transdermal absorptivity thereof is increased to improve anti-inflammatory and skin wrinkle reducing effects, and the sustained release of the active ingredient is realized to control skin irritancy.

For this purpose, the present invention provides an anti-inflammatory and skin wrinkle reducing cosmetic composition containing retinol stabilized by nano-emulsification, wherein a retinol polymer nanocapsule formed by adsorbing retinol with mesoporous polymer beads is nano-emulsified to a size of 50~200 nm using a mung bean MCT (medium chain triglyceride) extract and lecithin to stabilize the retinol.

Hereinafter, a method of dually stabilizing retinol will be described in detail.

First, retinol, an active ingredient, is adsorbed in mesoporous polymer beads having excellent biocompatibility to prepare a retinol polymer nanocapsule for primarily stabilizing the retinol. The mesoporous polymer beads may be made of a porous polymer material having excellent biocompatibility, and, preferably, may be made of polymethylmethacrylate crosslinked with ethyleneglycol dimethacrylate.

In this case, mesoporous polymer particles having a size of 50~500 nm, preferably 200~300 nm, and more preferably 200 nm may be used as the mesoporous polymer beads for adsorbing retinol. The particle sizes of the mesoporous polymer beads captured with retinol are adjusted in the following emulsification process. The reason for this is that it is difficult to capture retinal when extremely small mesoporous polymer beads are used. The retinol, an active ingredient, may be included in the retinal polymer nanocapsule in an amount of 0.5~10 wt % although the amount thereof is not limited.

Subsequently, the primarily stabilized retinol polymer nanocapsule is added to a composition including glycerin, tocopheryl acetate, butylated hydroxyanisole, a mung bean MCT (medium chain triglyceride) extract, cholesterol, lecithin and purified water to prepare a nano-emulsion composition for secondarily stabilizing the retinol. Thereafter, the nano-emulsion composition is formed into a nano-emulsion having a size of 50~200 nm, preferably, 70~100 nm using a high-pressure homogenizer to stabilize the retinol.

The lecithin may be at least one selected from the group consisting of hydrogenated lecithin, phosphatidylcholine, phospholipid, hydrogenated lysophosphatidylcholine, hydrogenated lysolecithin, hydroxylated lecithin, and unsaturated lecithin. Preferably, the lecithin may be hydrogenated lysolecithin.

According to an embodiment of the present invention, the mung bean MCT extract is prepared by mixing mung bean with caprylic/capric triglyceride and then extracting the mixture at about 80° C. for 3~5 hours. The anti-inflammatory efficacy and skin wrinkle reducing efficacy of the mung bean MCT extract are improved in a retinol-containing emulsion, and the mung bean MCT extract contributes to the stabilization of the nano-emulsion, and thus the addition of the mung been MCT extract is important in the manufacture of anti-inflammatory and skin wrinkle reducing cosmetics in which the stability of retinol is improved. The present invention is characterized in that retinol is not directly applied to the skin by adsorbing retinol in a polymer nanocapsule, but applied to the skin by emulsifying the polymer nanocapsule adsorbed with retinol. Thus, retinol, which is an unstable active ingredient, is more stabilized to maintain titer for a long period of time, and retinol is nano-emulsified to improve the skin permeability of cosmetics.

According to an embodiment of the present invention, the nano-emulsion supporting the polymer nanocapsule adsorbed with retinol may be prepared by mixing the retinol-adsorbed polymer nanocapsule with a nano-emulsion composition including 1~60 wt % of glycerin, 0.5~1 wt % of tocopheryl acetate, 0.03~0.05 wt % of butylated hydroxyanisole, 1~12 wt % of a mung bean MCT (medium chain triglyceride) extract, 1~2 wt % of cholesterol, 0.1~10 wt % of a retinol polymer nanocapsule, 1~3 wt % of hydrogenated lysolecithin and residual purified water.

The stabilized retinol may be included in an amount of 0.0001 wt %~50 wt % based on the total amount of the cosmetic composition. The cosmetic composition may be applied in the formulation of soft wash, nutritive wash, massage cream, nutritive cream, skin packs, gel, skin cream, lipstick, makeup base, foundation, shampoo, rinse, body cleanser, soap, toothpaste, oral purifier, lotion, ointment, patches, or spray.

According to an embodiment of the present invention, the stabilized retinol of the present invention may be prepared by the following method including the steps of: (A) (a1) adding mesoporous polymer beads having a particle size of 50 nm to 500 nm to ethanol to prepare a first mixture, stirring the first mixture, mixing an antioxidant (butylated hydroxytoluene) with the first mixture to prepare a second mixture, and then dissolving the second mixture, (a2) adding retinol (vitamin A) to the second mixture to prepare a third mixture, completely dissolving the third mixture, mixing the third mixture with distilled water to prepare a mixed solution, and then stirring the mixed solution, (a3) filtering and drying the mixed solution under reduced pressure to prepare a retinol-adsorbed polymer nanocapsule; (B) (b1) heating glycerin, and then mixing the heated glycerin with tocopheryl acetate, butylated hydroxyanisole and a mung bean MCT extract to prepare a fourth mixture while dissolving the fourth mixture, (b2) adding cholesterol to the fourth mixture to prepare a fifth mixture, dissolving the fifth mixture, and then adding the retinol-adsorbed polymer nanocapsule to the fifth mixture to prepare a sixth mixture, (b3) adding hydrogenated lysolecithin to the sixth mixture to prepare a seventh mixture, dissolving the seventh mixture, adding purified water to the seventh mixture to prepare a mixed solution, and then stirring the mixed solution to prepare a nano-emulsion composition; and (C) forming the nano-emulsion composition into a nano-emulsion having a size of 50~200 nm using a high-pressure homogenizer (microfluidizer) to stabilize retinol.

In the step (A), the retinol-adsorbed polymer nanocapsule is prepared using the mesoporous polymer beads having a size of 50 nm to 500, but the size of the polymer nanocapsule may be adjusted in the nano-emulsification of the step (C). Therefore, according to an embodiment of the present invention, the size of the polymer nanocapsule existing in the nano-emulsion may be adjusted to 40~180 nm.

When the size of the polymer nanocapsule is less than 40 nm, there is a problem in that it excessively deeply permeates into the skin, and thus it is difficult to discharge it to the outside of the skin. When the size thereof is more than 180 nm, there is a problem in that the particle size of the nano-emulsion increases, and thus the transdermal absorptivity thereof decreases. The polymer nanocapsule slowly emits effective ingredients while staying in the intermediate layer of the skin, and is pushed out to the outer layer of the skin according to the turnover period, and is thus removed from the skin together with a horny layer stripped from the skin.

In the method, the nano-emulsion composition may include 1~60 wt % of glycerin, 0.5~1 wt % of tocopheryl acetate, 0.03~0.05 wt % of butylated hydroxyanisole, 1~12 wt % of a mung bean MCT (medium chain triglyceride) extract, 1~2 wt % of cholesterol, 1~10 wt % of a retinal polymer nanocapsule, 1~3 wt % of hydrogenated lysolecithin, and purified water.

As the result of evaluating the titer maintaining ability to the stabilized retinol using HPLC, it can be ascertained that the content of the retinol stabilized by the present invention is maintained at 100% or more for 28 days at room temperature (25° C.), and is maintained at 90% or more for 28 days even at high temperature (45° C.), and thus the stability of retinol is excellent. As the result of evaluating the effect of preventing the expression of TNF-α and IL-1α in order to ascertain the irritancy relaxation effect, it can be ascertained that, when a HaCaT cell strain is treated with the stabilized retinol of the present invention, the expression of cytokine was remarkably reduced. As the result of ascertaining the influence of the stabilized retinol on the expression of a procollagen mRNA, it can be ascertained that, when the procollagen mRNA was treated with the stabilized retinol, the expression of COL1A1 was remarkably increased. Consequently, it can be ascertained that the stabilized retinol according to the present invention is very effective at weakening skin irritancy and improving a skin wrinkle reducing effect.

MODE FOR INVENTION

Examples

Hereinafter, the present invention will be described in more detail with reference to the following Examples and Test Examples. However, the scope of the present invention is not limited to these Examples.

Preparation Example 1

Preparation of Retinol-Absorbed Polymer Nanocapsule 50 g of mesoporous polymer beads having a size of 10 nm and made of polymethylmethacrylate crosslinked with ethyleneglycol dimethacrylate was added to ethanol in a 5 L beaker, was stirred for 40 minutes or more using an agi mixer, was mixed with 2 g of butylated hydroxytoluene, and was then dissolved to prepare a first mixed solution. Subsequently, 40 g of retinal (vitamin A) was added to the first mixed solution, was completely dissolved, was mixed with purified water, and was then stirred for 5 minutes or more to prepare a second mixed solution. Subsequently, the second mixed solution was filtered under reduced pressure to obtain retinol-adsorbed mesoporous polymer beads, and then the retinol-adsorbed mesoporous polymer beads were vacuum-dried at 45° C. (yield: 96.78%).

Example 1

Preparation of Nano-Emulsion Supported with Retinol-Adsorbed Polymer Nanocapsule 600 g of glycerin was put into a 2 L beaker, was heated to 70° C., was mixed with 10 g of tocopheryl acetate, 0.05 g of butylated hydroxyanisole and 150 g of a mung bean MCT extract, and was then dissolved at a constant temperature to prepare a first mixed solution. Subsequently, 20 g of cholesterol (manufactured by Solvay Corporation in Germany) was added to the first mixed solution and then dissolved, was mixed with 80 g of the retinol-adsorbed polymer nanocapsule and 30 g of hydrogenated lysolecithin (PC 70%), and was then completely dissolved at 65° C. to prepare a second mixed solution. Subsequently, 200 g of purified water was added to the second mixed solution and stirred for 50 minutes, and was then passed through a high-pressure homogenizer (microfluidizer, M-110F, Germany) at a pressure of 1,500 bar two times to prepare a nano-emulsion supported with the retinol-adsorbed polymer nanocapsule and having a size of 75 nm.

Preparation Example 2

Preparation of Nano-Emulsion Supported with Retinol

A nano-emulsion was prepared in the same manner as in Example 1, except that 30 g of retinol (98% solution) was added instead of the retinol-adsorbed polymer nanocapsule of Preparation Example 1.

Preparation Example 3

Preparation of Nano-Emulsion Supported with Retinol

A nano-emulsion was prepared in the same manner as in Example 1, except that the mung bean MCT extract was not added.

Test Example 1

Evaluation of Titer Maintaining Ability of Retinol

The titer of the retinol stabilized in Example 1 was evaluated at room temperature (25° C.) and high temperature (45° C.). Further, the titer of the stabilized retinol immediately prepared in Preparation Examples 1 and 3 and the titer of the retinol left at 45° C. for 5 weeks were evaluated by measuring the absorbance thereof using HPLC (at 325 nm).

1) Preparation of Test Solution 2500 IU of retinol was dissolved in 100 mL of methanol to obtain 100 mL of solution, and then 10 mL of the solution was diluted ten times, and, if necessary, filtered to prepare a test solution.

2) Preparation of Standard Solution 10 mL of the solution containing 100 mL of retinol was added to methanol to prepare 100 mL of a solution. This solution was used as a standard solution.

3) Analysis Method

A column filled with C18 was used, and an ultraviolet absorptiometer having a wavelength of 325 nm was used as a detector. 90% ethanol was used as a mobile phase under a condition of a flow rate of 1.0 mL/min.

Figure 2:
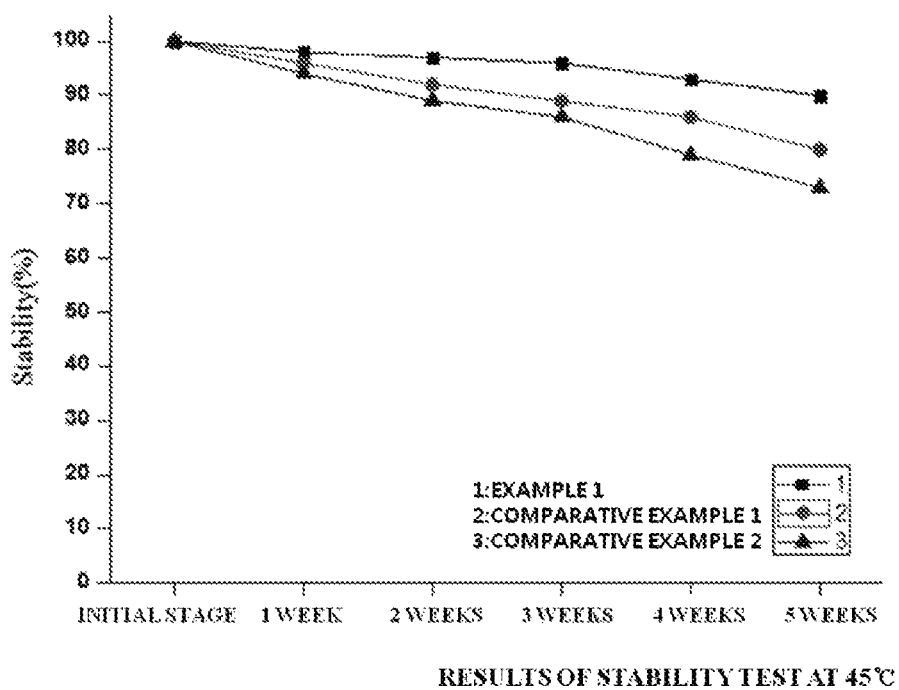

The results thereof are shown in FIGS. 1 and 2.

As shown in FIG. 1, as the result of measuring the contents of retinol at room temperature (25° C.) and high temperature (45° C.) for 35 days, it can be ascertained that the content of the retinol stabilized in Example 1 was maintained at 100% or more at low temperature, and was maintained at 90% or more even at high temperature, and thus the stability of the retinol was excellent. Further, as shown in FIG. 2, it can be ascertained that the retinol titer maintaining ability in Comparative Example 1 in which secondary emulsification was not performed or the retinol titer maintaining ability in Comparative Example 2 in which a mung bean MCT extract was not added is low compared to the retinol titer maintaining ability in Example 1. That is, it can be ascertained that the retinol titer maintaining ability is greatly improved by dual stabilization attributable to secondary emulsification and by the addition of a mung bean MCT extract.

The efficacy test was carried out as follows in order to evaluate the physiological activity of stabilized retinol.

Cell Culture

HaCaT (human keratinocytes cell line) was used as a test cell, and was cultured in a DMEM (Dulbecco's modified Eagle's medium, Invitrogen) medium including 5% of $CO_2$, 10% of a fetal bovine serum (FBS, Lonza) and 50 μg/mL of streptomycin (Sigma).

Measurement of Expression of Cytokine RNA Separation

In order to analyze RNA, total RNA was extracted from a cultured cell using a trizol reagent (invitrogen, USA). The purity and noncrystallinity of RNA was ascertained by measuring the ratio of $A_{260}$ nm/$A_{280}$ nm, and the yield of RNA was ascertained by measuring absorbance at 260 nm.

Reverse Transcriptase—Polymerase Chain Reaction (RT-PCR)

3 μg of total RNA was added to an oligo dT 15 primer (500 ng/μl, dNTP (10 mM), a RTase inhibitor (40 U/μl), a powerscript II RTase (Clontech, USA), and then the mixture was primer-annealed at 25° C. for 10 minutes to synthesize cDNA at 42° C. for 60 minutes, and then the cDNA was denatured at 95° C. for 5 minutes using a RTase. In the polymerase chain reaction (PCR), in order to amplify TNF-α, IL-1α, COL1A1 and GAPDH from the cDNA, 3 μl of cDNA, 5 μl of a 10×taq polymerase, 2 μl of a 2.5 mM dNTP, 2 μl of a 10 pmol primer and 0.5 μl of a taq polymerase were mixed with each other, and then distilled water was added to the mixture to prepare 50 μl of a mixed solution, and then the amplification was performed. Primer ranks are given in Table 1 below. The product obtained by the PCR was electrophoresed in a 1% agarose gel and then observed by an image analyzer (UGEN, U: Genius), and the density of each band was measured using a densitometric program (Gene Tools from Syngene). The stabilized retinol (0.2%) of Preparation Example 2 was used as a comparative example.

TABLE 1

| Gene | Primer |
| --- | --- |
| GAPDH | Forward 5'-AAC GAA TTT GGT CGA ACA CC-3'<br>Reverse 5'-TCA GGA GGG ATT CAG TC-3' |
| TNF-α | Forward 5'-CAG AGG GAA GAG TTC CCC AG-3'<br>Reverse 5'-CCT TGG TCT GGT AGG AGA CG-3' |
| IL-1α | Forward 5'-GTC TCT GAA TCA GAA ATC CTT CTA TC-3'<br>Reverse 5'-CAT GTC AAA TTT CAC TGC TTC ATC C-3' |
| COL1A1 | Forward 5'-AGC CAG CAG ATC GAG AAC AT-3'<br>Reverse 5'-TCT TGT CCT TGG GGT TCT TG-3' |

Zymography

Protein was separated using a cell lysis buffer [50 mM Tris-HCl (pH 8.0), 150 mM NaCl, 5 mM EDTA, 1% Triton X-100, and 1 mM PMSF], and the amount of protein was measured by Bradford protein assay, and then protein was used. An SDS-PAGE GEL including 2% gelatin (Fluka) was provided. Protein was mixed with a tris-glycine SDS buffer, and a reaction was carried out at room temperature for 10 minutes. In this case, heating was not performed. A gel was loaded with protein and a 1×tris-glycine SDS running buffer. Subsequently, the gel was immersed in a 1× zymogram renaturing buffer, and then slowly stirred at room temperature for 30 minutes. Thereafter, the gel was introduced into a 1× zymogram developing buffer, and a reaction was carried out at room temperature for 30 minutes, and then the 1× zymogram developing buffer was replaced by a clean 1× zymogram developing buffer, and then the reaction product overnighted. Next day, the reaction product was stained by Coomassie blue R-250 (BIO-RAD) for 30 minutes, and was then destained.

Test Example 2

Test for Inhibiting the Expression of Cytokine

In order to evaluate the anti-inflammatory effect of the stabilized retinol of Example 1, the ability of retinal to inhibit the expression of cytokine was evaluated by the test method. That is, a keratin forming cell was irradiated with ultraviolet for increasing the expression of cytokine, and then the effect of retinal on inhibiting the expression of cytokine was ascertained using the stabilized retinol (0.2%) of Preparation Example 2 as Comparative Example 3. The results thereof are shown in FIG. 3.

Figure 3:
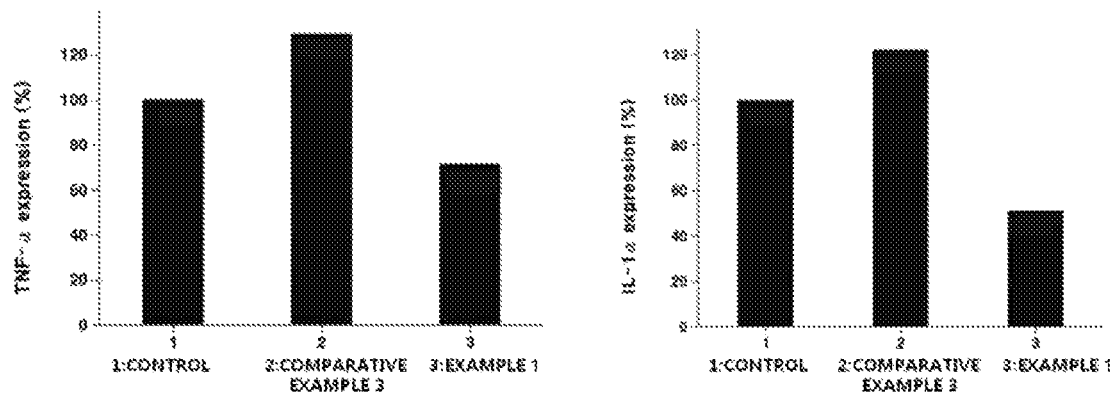
FIG. 3 is a graph showing the cytokine expression control ability of the stabilized retinol according to an embodiment of the present invention.
Figure 4:
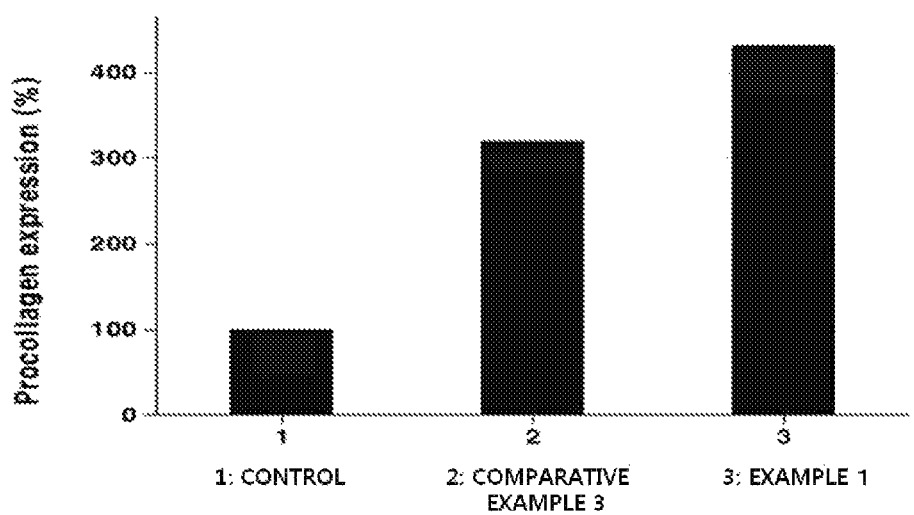
FIGS. 4 and 5 are graphs showing the collagen expression acceleration effect of the stabilized retinol according to an embodiment of the present invention.

As shown in FIG. 3, as the result of irradiating a keratin forming cell with ultraviolet for increasing the expression of cytokine and then evaluating the effects of the retinols of Example 1 and Comparative Example 3 on inhibiting the expression of cytokine, it can be ascertained that, when the retinol of Comparative Example 3 was used, the expression of both TNF-α and IL-1α was increased, but, when the retinol of Example 1 was used, the expression of both TNF-α and IL-1α was remarkably decreased.

Test Example 3

Test for Accelerating the Biosynthesis of Collagen

In order to ascertain whether the stabilized retinol of the present invention influences the expression of COL1A1 (type 1 procollagen), the amount of expressed COL1A1 was ascertained by performing RT-PCR. The results thereof are shown in FIG. 3a. It can be ascertained from FIG. 3a that, when the stabilized retinol of Example 1 was used, the amount of expressed COL1A1 was increased compared to when the retinol of Comparative Example 3 was used.

Effect of Retinol on the Expression of Procollagen Protein

Figure 5:
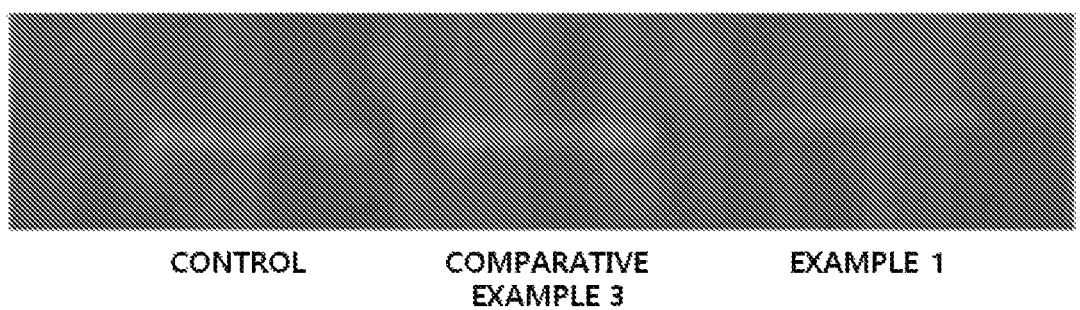

In order to ascertain whether the stabilized retinol of the present invention has something to do with the expression of a gelatin decomposition protein by ascertaining the effect of the retinol on the expression of procollagen mRNA, zymography was carried out. The results thereof are shown in FIG. 5. It can be ascertained from FIG. 5 that when the stabilized retinol of Example 1 was used, the level of expression of a MNP-2 protein for decomposing gelatin was decreased compared to when the retinol of Comparative Example 3 was used.

As ascertained in the Test Examples, it can be seen that the stabilized retinol according to the present invention has excellent titer maintaining ability, an anti-inflammatory effect and a skin wrinkle reducing effect.

Example 2

Preparation of Cream

A cosmetic composition, given in Table 2 below, was prepared using the stabilized retinol prepared in Example.

TABLE 2

| Composition (wt %) | Ex. 2 | Comp. Ex. 4 | Comp. Ex. 5 |
|---|---|---|---|
| Retinol emulsion (Ex. 1) | 3.00 | — | — |
| Retinol crystal | — | 0.04 | 0.03 |
| Glycerin | 1.00 | 1.00 | 1.00 |
| Butyleneglycol | 2.00 | 2.00 | 2.00 |

TABLE 2-continued

| Composition (wt %) | Ex. 2 | Comp. Ex. 4 | Comp. Ex. 5 |
|---|---|---|---|
| Arachidyl alcohol/behenyl alcohol/arachidyl glucoside | 2.50 | 2.50 | 2.50 |
| Glyceryl stearate | 0.50 | 0.50 | 0.50 |
| PEG-4 olyvate | 0.50 | 0.50 | 0.50 |
| Caprylic/capric triglyceride | 5.00 | 4.00 | 5.00 |
| Cholesterol/behenyl/octyldodecyllauroyl glutamate | 1.00 | 1.00 | 1.00 |
| *Macadamia integrifolia* seed oil | 1.00 | 1.00 | 1.00 |
| Dimethicone | 0.50 | 0.50 | 0.50 |
| Cyclopentasiloxane/cyclohexasiloxane | 2.00 | 2.00 | 2.00 |
| Cetearyl alcohol | 1.00 | 1.00 | 1.00 |
| Mineral oil | 2.50 | 2.50 | 2.50 |
| Disodium EDTA | 0.03 | 0.03 | 0.03 |
| BHT | 0.05 | 0.05 | 0.05 |
| Tocopheryl acetate | 0.30 | 0.30 | 0.30 |
| Panthenol | 0.20 | 0.20 | 0.20 |
| Ethylhexyl methoxycinnamate | 0.20 | 0.20 | 0.20 |
| Propyl paraben | 0.10 | 0.10 | 0.10 |
| Methyl paraben | 0.20 | 0.20 | 0.20 |
| Perfume | 0.01 | 0.01 | 0.01 |
| Purified water | 76.41 | 80.37 | 79.38 |

Test Example 4

Formulation Stability Test

The formulation stability of the retinols of Example 2 and Comparative Examples 4 and 5 was evaluated in the same manner as in Test Example 1. The results thereof are shown in FIG. 6.

Figure 6:
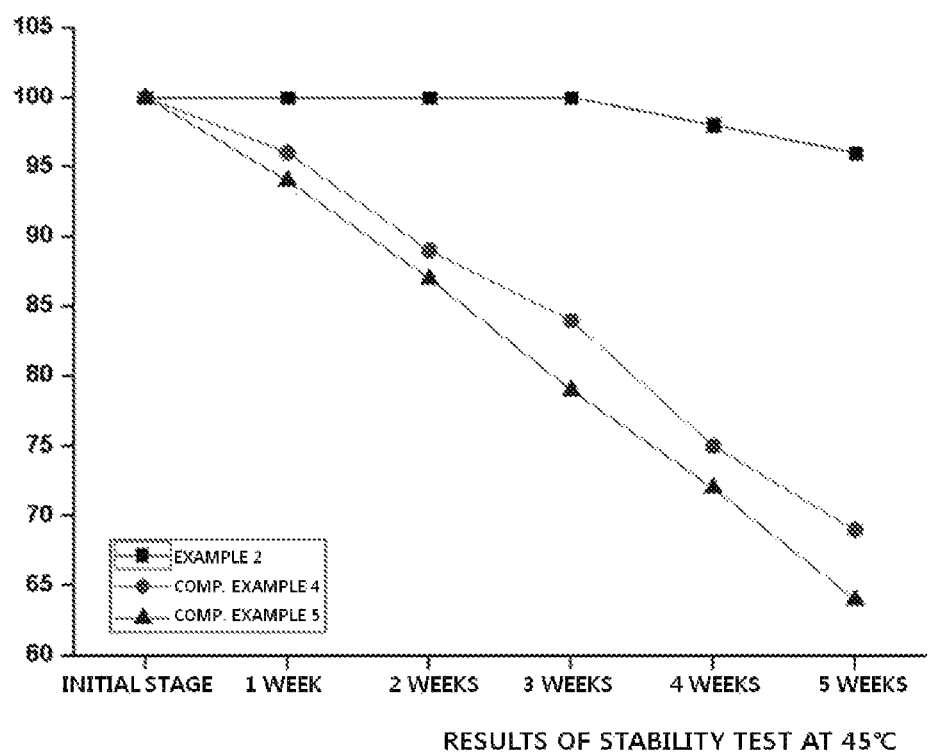
FIG. 6 is a graph showing the stability of a formulation containing the stabilized retinol according to an embodiment of the present invention.

As shown in FIG. 6, it can be ascertained that the stabilized retinol of Example 2 exhibited excellent formulation stability.

Test Example 5

Discoloration Test

The formulation discoloration tests of the cosmetic compositions prepared in Example 2 and Comparative Examples 4 and 5 were carried out as follows.

Figure 7:
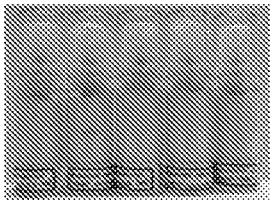
FIG. 7 is a photograph showing the test results of stability of the cosmetic composition containing the stabilized retinol according to an embodiment of the present invention.
Figure 7:
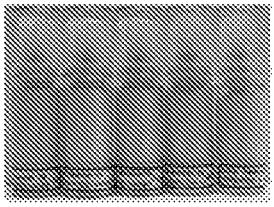
Figure 7:
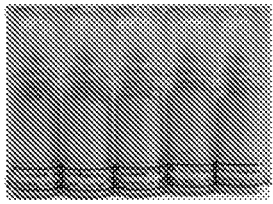
Figure 7:
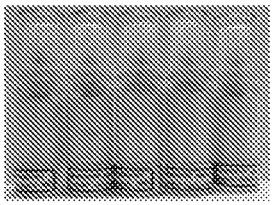
Figure 7:
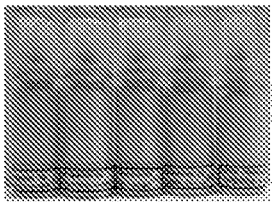
Figure 7:
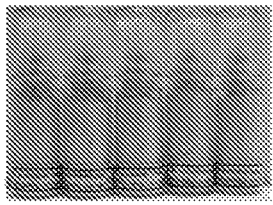
Figure 7:
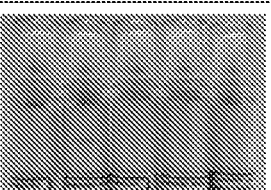
Figure 7:
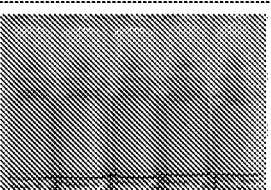
Figure 7:
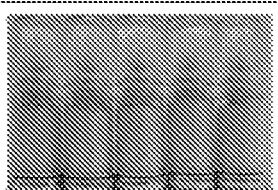
Figure 7:
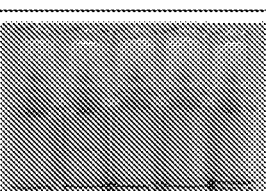
Figure 7:
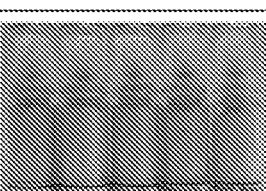
Figure 7:
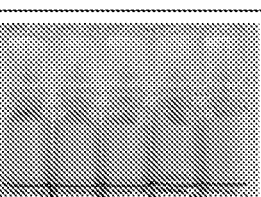
Figure 7:
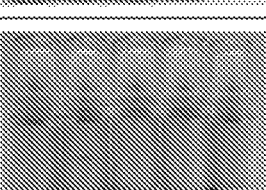
Figure 7:
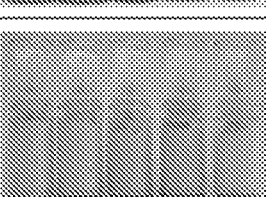
Figure 7:
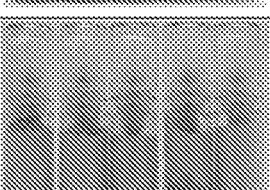
Figure 7:
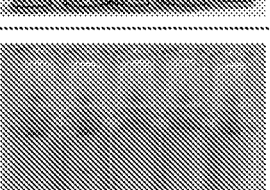
Figure 7:
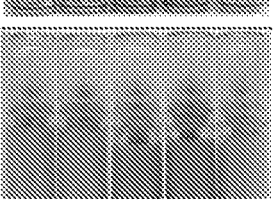
Figure 7:
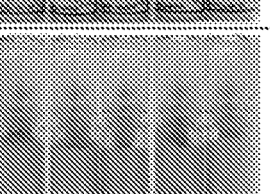

The stability tests of the cosmetic compositions prepared in Example 2 and Comparative Examples 4 and 5 were carried out at 4° C., 25° C., 45° C. and 50° C. for 5 weeks in the presence of sunlight, and the results thereof are shown in FIG. 7 and Table 3 below.

TABLE 3

| | Condition | Initial | 1 week | 2 weeks | 3 weeks | 4 weeks | 5 weeks |
|---|---|---|---|---|---|---|---|
| Ex. 2 | 4° C. | − | − | − | − | − | − |
| | 25° C. | − | − | − | − | − | − |
| | 45° C. | − | − | − | − | − | − |
| | 50° C. | − | − | − | − | + | + |
| | sunlight | − | − | − | − | − | − |
| Comp. Ex. 4 | 4° C. | − | − | − | − | − | − |
| | 25° C. | − | − | − | − | − | − |
| | 45° C. | − | − | − | ++ | ++ | ++ |
| | 50° C. | − | − | ++ | ++ | ++ | +++ |
| | sunlight | | | | | | |
| Comp. Ex. 5 | 4° C. | − | − | − | − | − | − |
| | 25° C. | − | − | − | − | − | − |
| | 45° C. | + | + | ++ | ++ | +++ | +++ |
| | 50° C. | + | ++ | ++ | +++ | +++ | +++ |
| | sunlight | − | − | − | − | − | − |

(−: not discolored, ± < +: degree of discoloration)

As shown in FIG. 7 and Table 3 above, it can be ascertained that the cosmetic composition of Example 2 including the stabilized retinol of the present invention has excellent stability compared to the cosmetic compositions of Comparative Examples 4 and 5.

Test Example 6

Evaluation of Skin Irritancy

The skin wrinkle reducing effects of the cosmetic compositions prepared in Example 2 and Comparative Examples 4 and 5 were measured as follows.

Forty women in their thirties were classified into three groups (experimental group, control group 1 and control group 2). In the experimental group, the cosmetic composition of Example 2 was applied onto the eye rims in an amount of 0.2 g every night for 12 weeks, and in the control groups 1 and 2, each of the cosmetic compositions of Comparative Examples 4 and 5 was applied onto the eye rims in an amount of 0.2 g every night for 12 weeks, and then the wrinkles formed on the eye rims were measured using ARAMO TS (Aram Hubis, Korea) to evaluate the wrinkle reducing effects of the cosmetic compositions. The results thereof are given in Tables 4 and 5 below.

TABLE 4

| | Numerical values of measured wrinkles | | | | | | | | |
|---|---|---|---|---|---|---|---|---|---|
| | Ex. 2 | | | Comp. Ex. 4 | | | Comp. Ex. 5 | | |
| | T0 | T12 | Difference | T0 | T12 | Difference | T0 | T12 | Difference |
| Examinee 1 | 33 | 28 | 5 | 36 | 35 | 1 | 33 | 30 | 3 |
| Examinee 2 | 36 | 26 | 10 | 37 | 37 | 0 | 36 | 29 | 7 |
| Examinee 3 | 37 | 29 | 8 | 32 | 31 | 1 | 37 | 36 | 1 |
| Examinee 4 | 35 | 30 | 5 | 33 | 35 | −2 | 35 | 32 | 3 |
| Examinee 5 | 33 | 31 | 2 | 38 | 33 | 5 | 33 | 31 | 2 |
| Examinee 6 | 35 | 30 | 5 | 35 | 35 | 0 | 35 | 28 | 7 |
| Examinee 7 | 37 | 34 | 3 | 33 | 37 | −4 | 37 | 35 | 2 |
| Examinee 8 | 36 | 32 | 4 | 34 | 34 | 0 | 36 | 35 | 1 |
| Examinee 9 | 33 | 28 | 5 | 36 | 35 | 1 | 33 | 30 | 3 |
| Examinee 10 | 37 | 33 | 4 | 37 | 37 | 0 | 37 | 34 | 3 |
| Average | 35.2 | 30.1 | 5.1 | 35.1 | 34.9 | 0.2 | 35.2 | 32.0 | 3.2 |

TABLE 5

| | Degree of irritancy | |
|---|---|---|
| | Ex. 2 | Comp. Ex. 5 |
| Examinee 1 | 0 | 3 |
| Examinee 2 | 0 | 4 |
| Examinee 3 | 0 | 3 |
| Examinee 4 | 1 | 2 |
| Examinee 5 | 0 | 3 |
| Examinee 6 | 1 | 3 |
| Examinee 7 | 0 | 2 |
| Examinee 8 | 0 | 2 |
| Examinee 9 | 0 | 3 |

TABLE 5-continued

| | Degree of irritancy | |
|---|---|---|
| | Ex. 2 | Comp. Ex. 5 |
| Examinee 10 | 0 | 1 |
| Average | 0.2 | 2.6 |

(0: irritancy does not exist, 5: not used due to severe irritancy)

From the results, it can be ascertained that, when the cosmetic composition of Example 2 was used for 12 weeks, the number of skin wrinkles was decreased by 5.1 (14.49%), and thus the wrinkle reducing effect of the cosmetic composition of Example 1 was improved 25.4 times that (0.24 (0.57%)) of the cosmetic composition of Comparative Example 4. Further, it can be ascertained that the wrinkle reducing effect of the cosmetic composition of Example 1 was improved 1.6 times that (3.2 (9.09%)) of the cosmetic composition of Comparative Example 5.

Further, as the result of observing examinees using the cosmetic compositions of Example 2 and Comparative Example 5 by questions, when the cosmetic composition of Comparative Example 5 was used, a large number of examinees complained of irritancy, but, when the cosmetic composition of Example 2 was used, two examinees felt slight irritancy, and other examinees did not feel irritancy. Therefore, from the results, it can be ascertained that the stabilized retinol of the present invention exhibits an excellent wrinkle reducing effect and an excellent irritancy relaxing effect.

Industrial Applicability

The present invention provides a technology for using retinol (vitamin A), a bioactive component, in low-irritation cosmetics for improving a skin wrinkle reducing effect, wherein the retinol is primarily stabilized by adsorbing the retinol in mesoporous polymer particles, and is then secondarily stabilized by nano-emulsifying the retinol using a specific fat-soluble natural extract and lecithin.

The invention claimed is:
1. An anti-inflammatory and skin wrinkle reducing cosmetic composition containing retinol stabilized by nano- emulsification, wherein a retinol polymer nanocapsule formed by adsorbing retinol with mesoporous polymer beads is nano-emulsified to a size of 50-200 nm using a mung bean MCT (medium chain triglyceride) extract and lecithin to stabilize the retinol.

2. The cosmetic composition of claim 1, wherein the mesoporous polymer beads are made of polymethylmethacrylate crosslinked with ethyleneglycol dimethacrylate.

3. The cosmetic composition of claim 1, wherein the retinol, an active ingredient, is included in the retinol polymer nanocapsule in an amount of 0.5-10 wt % of the total composition.

4. The cosmetic composition of claim 1, wherein the lecithin is at least one selected from the group consisting of hydrogenated lecithin, phosphatidylcholine, phospholipid, hydrogenated lysophosphatidylcholine, hydrogenated lysolecithin, hydroxylated lecithin, and unsaturated lecithin.

5. The cosmetic composition of claim 1, wherein the stabilized retinol is included in an amount of 0.0001 wt % -50 wt % based on a total amount of the cosmetic composition.

6. The cosmetic composition of claim 1, wherein the formulation of the cosmetic composition is a soft wash, nutritive wash, massage cream, nutritive cream, skin pack, gel, skin cream, lipstick, makeup base, foundation, shampoo, rinse, body cleanser, soap, toothpaste, oral purifier, lotion, ointment, patch, or spray.

7. A method of stabilizing retinol, comprising the steps of:
(A) (a1) adding mesoporous polymer beads having a particle size of 50 nm to 500 nm to ethanol to prepare a first mixture, stirring the first mixture, mixing an antioxidant comprising butylated hydroxytoluene with the first mixture to prepare a second mixture, (a2) adding retinol to the second mixture to prepare a third mixture, mixing the third mixture with distilled water to prepare a mixed solution, and then stirring the mixed solution, (a3) filtering and drying the mixed solution under reduced pressure to prepare a retinol-adsorbed polymer nanocapsule;
(B) (b1) heating glycerin, and then mixing the heated glycerin with tocopheryl acetate, butylated hydroxyanisole and a mung bean MCT extract to prepare a fourth mixture (b2) adding cholesterol to the fourth mixture to prepare a fifth mixture, and then adding the retinal-adsorbed polymer nanocapsule to the fifth mixture to prepare a sixth mixture, (b3) adding hydrogenated lysolecithin to the sixth mixture to prepare a seventh mixture, adding purified water to the seventh mixture to prepare a mixed solution, and then stirring the mixed solution to prepare a nano-emulsion composition; and
(C) forming the nano-emulsion composition into a nano-emulsion having a size of 50-200 nm using a high-pressure homogenizer to stabilize retinal.

8. The method of claim 7, wherein the nano-emulsion composition comprises 1-60 wt % of glycerin, 0.5-1 wt % of tocopheryl acetate, 0.03-0.05 wt % of butylated hydroxyanisole, 1-12 wt % of a mung bean MCT (medium chain triglyceride) extract, 1-2 wt % of cholesterol, 1-10 wt % of a retinol polymer nanocapsule, 1-3 wt % of hydrogenated lysolecithin, and purified water wherein each wt % is based on a weight of the total composition.

9. The method of claim 8, wherein the mung bean MCT (medium chain triglyceride) extract is a caprylic/capric triglyceride extract of mung bean.

* * * * *